United States Patent [19]

Tustin

[11] Patent Number: 5,530,167
[45] Date of Patent: Jun. 25, 1996

[54] PROCESS FOR THE PREPARATION OF 1,4-BUTENEDIOL

[75] Inventor: Gerald C. Tustin, Kingsport, Tenn.

[73] Assignee: Eastman Chemical Company, Kingsport, Tenn.

[21] Appl. No.: 517,394

[22] Filed: Aug. 21, 1995

[51] Int. Cl.$^6$ .................................................. C07C 29/56
[52] U.S. Cl. ............................................ 568/857; 568/860
[58] Field of Search ..................................... 568/857, 860

[56] References Cited

FOREIGN PATENT DOCUMENTS 54-73710   6/1979   Japan .

*Primary Examiner*—Samuel Barts
*Attorney, Agent, or Firm*—J. Frederick Thomsen; Harry J. Gwinnell

[57] ABSTRACT

Disclosed is an improved process for the preparation of 1,4-butenediol by the hydrolysis of 3,4-epoxy-1-butene (EpB) wherein a mixture of EpB and water is contacted with a catalyst comprising a catalyst support material an copper in a positive valence state.

7 Claims, No Drawings

PROCESS FOR THE PREPARATION OF 1,4-BUTENEDIOL

This invention pertains to a process for the preparation of 1,4-butenediol from 3,4-epoxy-1-butene (EpB). More specifically, this invention pertains to a heterogeneous process for the hydrolysis of EpB to 1,4-butenediol wherein a mixture of EpB and water is contacted with a catalyst comprising a catalyst support material and copper in a positive valence state.

1,4-butanediol (BDO) is an important industrial chemical. For example, it is used in substantial quantities as a monomer for a variety of polyesters and polyurethanes. It also is used to prepare the useful industrial solvent tetrahydrofuran and can be converted to γ-butyrolactone which in turn can be converted into polyvinylpyrrolidone and N-methylpyrrolidinone.

Most of the BDO produced commercially is made by the reaction of acetylene with formaldehyde followed by hydrogenation. This procedure suffers from the use of the relatively expensive and dangerous acetylene. Some BDO also is produced by the reaction of acetic acid, oxygen and butadiene to produce 1,4-diacetoxy-2-butene which is then hydrogenated and hydrolyzed. This process suffers from the number of steps involved and from the co-production of 3,4-diacetoxy-1-butene. Other known routes for the preparation of BDO include butadiene chlorination followed by basic hydrolysis and hydrogenation (producing a mixture of isomers and salts), maleic anhydride hydrogenation (requiring severe operating conditions), and the rearrangement of propylene oxide to allyl alcohol followed by reaction with hydrogen and carbon monoxide to produce 4-hydroxybutyraldehyde which then is hydrogenated to BDO (requiring a large number of steps, one of which employs an expensive rhodium catalyst). A general need exists for a BDO process that is safe, inexpensive and simple.

The hydrogenation of 1,4-butenediol (also known as 3-butene-1,4-diol) is an attractive route to BDO, but no syntheses of 1,4-butenediol are known that are safe, efficient and inexpensive. EpB can be made efficiently from butadiene and oxygen, but no ways are known to efficiently hydrolyze EpB to a product abundant in 1,4-butenediol. A need exists for a process that efficiently hydrolyzes 3,4-epoxy-1-butene to a product abundant in 1,4-butenediol.

In *J. Am. Chem. Soc.* 104, 1658–1665 (1982), Ross et al. teach that acid-catalyzed hydrolysis of EpB produces a mixture containing 96% 3-butene-1,2-diol and only 4% 1,4-butenediol. This same reference leads one to expect even more 3-butene-1,2-diol to be produced with base-catalyzed hydrolysis since the related cyclohexadiene oxide yields 99% of the 1,2-diol upon base-catalyzed hydrolysis in the absence of other salts. Thus, neither acid nor base catalysis appears to be suitable for the hydrolysis of EpB to a product containing useful levels of the desired 1,4-butenediol.

In *Tetrahedron* 45, 7031–7040 (1989), Rao et al. teach that acidic, aqueous conditions can convert the desired 1,4-butenediol into the undesired 3--butene-1,2-diol. This reference suggests that acidic conditions may be undesirable under some hydrolysis conditions. A process that uses hydriodic acid or hydriodic acid plus a transition metal compound as catalysts for the hydrolysis of EpB to mixtures containing 1,4-butenediol is described in Japanese Kokai Patent No. Sho 54[11979]-79214. Under the optimum conditions reported, these conditions produced a diol mixture consisting of 53% 3-butene-1,2-diol (hereafter termed 1,2-butenediol) and 47% 1,4-butenediol (1,2-diol/1,4-diol ratio=1.15) with a total diol yield of only 58%. This process not only gives a poor yield, but has all of the corrosion and separation problems associated with the use of aqueous hydriodic acid.

Japanese Kokai 54[1979]-73710 teaches the use of both Cu(I) and Cu(II) salts as catalysts for the hydrolysis of EpB to mixtures rich in 1,4-butenediol. CuBr provided a mixture of butenediols having a 1,2-isomer to 1,4-isomer ratio=2.92. $CuBr_2$ provided a mixture of butenediols having a 1,2-isomer to 1,4-isomer ratio=4.71. These reactions not only exhibit poor selectivity to the desired 1,4-butenediol, but reaction times of about 50 hours are required for the reaction to reach completion. No means are provided to separate and recover the catalyst and the product from the reaction mixture.

The present invention provides a simple, efficient means for the selective hydrolysis of 3,4-epoxy-1-butene (EpB) to a mixture rich in 1,4-butenediol through the utilization of heterogeneous catalysts that can easily be separated from the product mixture and reused. The process of the invention comprises contacting a mixture of water and EpB with a supported copper catalyst comprising a catalyst support material and copper in a positive valence state at a hydrolysis effective temperature. Unlike catalysts of the prior art, the catalyst used in the present process is separated easily from the liquid reaction products. The hydrolysis of EpB by means of the heterogeneous process of this invention results in improved selectivity to the desired 1,4-butenediol.

The catalysts useful in the present invention are a combination of a catalyst support material and a form of copper in a positive valence state, i.e., Cu(I) (cuprous) and/or Cu(II) (cupric) ions. The copper [Cu] content of the catalysts may range from about 0.1 to 10 weight percent, preferably about 2 to 5 weight percent, based on the total dry weight of the catalyst. One purpose of the support is to provide a high dispersion of catalytically active copper sites while keeping significant amounts of copper from dissolving in the aqueous medium. For this purpose, a wide variety of support materials are satisfactory. They include silica, alumina, silica-alumina, titania ($TiO_2$), carbon, magnesia (MgO) and zeolite materials. The preferred support materials are silica, alumina and zeolite materials. The most preferred materials are certain zeolite materials. Preferred zeolites are faujasite-type zeolites and L-type zeolites. The most preferred faujasite-type is zeolite Y containing sodium or, more preferably, lithium ions prior to copper exchange.

The nature of the copper salt used to prepare the supported positive valence state copper is not critical and may vary considerably depending on the nature of the support and whether a prereduction step is used before the hydrolysis. When non-zeolite supports, e.g., silica, alumina and silica-alumina, are used, it is preferable to use a copper(I) salt stabilized as an ammonia complex in aqueous solution. CuCl or CuBr in aqueous ammonia are satisfactory. The catalyst may be prepared by impregnating the support with the aqueous ammonia-copper(I) solution and then evaporating the solvent. Non-zeolite materials prepared in this way generally are more selective catalysts than those prepared by impregnating the same supports with Cu(II) salts. If Cu(II) salts are used in combination with a non-zeolite support, a prereduction in 1–2% hydrogen in nitrogen at 300° C. often will improve the initial performance of the catalyst.

When zeolite materials are used as supports, the copper may be supported by either exchange or by impregnation. The exchange method is preferred, and either Cu(I) salts in aqueous ammonia or Cu(II) salts in water or in aqueous ammonia may be used. The use of aqueous solutions of Cu(II) salts for the exchange into the zeolite is preferred. The exchange of copper salts into zeolites is well-known to those skilled in the art. Typically, an aqueous solution containing about 0.01 mole soluble copper(II) salt per liter of solution is contacted with the zeolite for about 2 hours at ambient temperature with the use of about 100 mL of the exchange solution per gram of zeolite. Generally, the exchanged zeolite is then washed with water. About 50 mole percent of the exchangeable ions in the zeolite (generally sodium ions) are replaced with copper ions under the above conditions. When copper(II) salts are used, one copper ion replaces about two alkali metal ions. Satisfactory catalysts normally have between about 1 and 100 mole percent of their exchangeable ions exchanged with copper ions.

The copper-containing catalysts useful in the present invention may be in pellet form or powdered form although higher rates generally result when the powdered form is used. The selectivity of the copper-containing catalysts may be improved by contacting the catalyst with a source of ammonia. Equilibration of the copper-containing catalyst prepared as described above with vapor from an aqueous ammonia solution is an excellent way to add the correct small amount of ammonia required to promote the copper catalysts without adversely affecting the hydrolysis selectivity through the reaction excessive amounts of basic ammonia solution with 3,4-epoxy-1-butene. The resulting catalysts are a combination of a catalyst support material, copper in a positive valence state and ammonia.

The process may be carried out as a heterogeneous, liquid phase process wherein one of the above-described supported copper catalysts is contacted with 3,4-epoxy-1-butene and water. In liquid phase, batch operation of the process, the catalyst typically is present in a concentration of about 1 to 50 weight percent, preferably about 5 to 10 weight percent, based on the total weight of the initial reaction mixture. Although liquid phase operation is preferred, operation of the process in the vapor phase is within the scope of the present invention. The reactive materials (water and EpB) may be employed in the process in an water:EpB weight ratio in the range of about 100:1 to 1:1, preferably about 20:1 to 5:1. Excessively high concentrations of EpB lead to the formation of larger amounts of oligomeric by-products whereas very dilute concentrations of EpB make recovery and purification of the products difficult and expensive. The process optionally may be carried out in the presence of an inert solvent although the use of a solvent usually is not preferred. Examples of such non-reactive solvents include nitriles such as acetonitrile, ketones such as acetone and ethers such as tetrahydrofuran.

The process of this invention may be carried out at temperatures ranging between about 10 and about 80° C. At lower temperatures the rate of uncatalyzed or spontaneous hydrolysis is faster than the rate of the supported copper catalyzed hydrolysis resulting in poor selectivity and low rate. Higher temperatures provide higher rates but do not provide higher selectivity. Volatility of the EpB at higher temperatures requires the use of elevated pressure to prevent the loss of unreacted EpB. Usually, the reaction is performed at atmospheric pressure and ambient temperature. The reaction is exothermic and, when the reactants and catalyst are mixed in the preferred amounts at ambient temperature, the temperature of the reaction typically increases by 10–15° C. Observation of the temperature rise from and eventual return to ambient temperature provides a convenient way to monitor the reaction when the reaction is performed in the batch mode. Often an induction period of between several minutes and several hours before the catalyst becomes appreciably active occurs when catalysts are used initially, especially when the catalyst is prepared from Cu(II). The process can be operated as a continuous or semi-continuous process by passing the reactants over one or more fixed beds of the catalyst. The catalyst normally is used in such fixed beds in a pelletized or other extruded or shaped form. The process of the invention consumes essentially all of the 3,4-epoxy-1-butene. Extended contact of the catalyst with the product does not alter the selectivity to 1,4-butenediol. The catalyst may be readily separated and recovered from the liquid products by simple filtration or centrifugation. Liquid products may be recovered by distillation. The recovered catalyst may be washed with water or other solvents to facilitate the removal of trace amounts of products, or it may be used again without washing. Induction periods usually are shorter or do not occur with subsequent use of the catalysts. The initial induction period can be eliminated by prereduction of the catalyst in 1–2% hydrogen in an inert gas such as nitrogen at 200°–300° C.

The process provided by my invention is further illustrated by the following examples. The hydrolysis reactions were performed in a three-necked, 500-mL, round-bottom flask equipped with an overhead stirrer, a nitrogen inlet (nitrogen pressure relieved through an oil bubbler) and, except for the experiment of Example 1, a thermocouple. The zeolite exchange reactions were performed in a 4-liter Erlenmeyer flask using magnetic stirring. Gas chromatography (GC) analyses were performed on a Hewlett-Packard Model 5890 gas chromatograph using a 30 meter long by 0.32 mm inside diameter DB-5 column (film thickness=1,0 micron) using p-xylene as an internal standard. The chromatograph was programmed at 40° C. for 3 minutes, 10° C. per minute to 120° C., 120° C. for 2 minutes, 20° C. per minute to 230° C. and 230° C. for 11.5 minutes.

EXAMPLE 1

This example illustrates the process of the invention using a non-zeolitic support, the stability of the product mixture after extended contact with the catalyst and the reuse of the catalyst.

Silica gel (40.0 g, Aldrich Merck grade 60) was impregnated with a solution of CuCl (2.00 g) dissolved in about 100 mL concentrated aqueous ammonia solution. The solvent was evaporated on a steam bath and the catalyst was dried further in an oven at 80C overnight.

The entire light blue catalyst was slurried in water (100 mL) and EpB (5.0 g) was added. The reaction mixture was stirred under a static nitrogen atmosphere. After stirring for 45 minutes, the vessel containing the reaction mixture was noticeably warm to the touch. After 6.5 hours of stirring, the stirrer was stopped, and the catalyst was allowed to settle. An aliquot of the liquid portion was removed and analyzed by GC. The product contained no EpB, 3.55 weight percent 1,2-butenediol and 1.79 weight percent 1,4-butenediol. The remainder of the reaction mixture was allowed to stir for an additional 24 hours in contact with the catalyst, and another aliquot was removed and analyzed by GC. The second aliquot contained no EpB, 3.64 wt % 1,2-butenediol and 1.87 wt % 1,4-butenediol.

The remaining reaction mixture was filtered (pH of filtrate=7), the green solid catalyst was washed with water (400 mL) and a fresh charge of water and EpB was added at 23° C. Within 20 minutes the temperature of the reaction mixture was 30° C. An aliquot was analyzed after a total of one hour reaction time and contained no 3,4-epoxy-1-butene, 3.76 weight percent 1,2-butenediol and 1.50 weight percent 1,4-butenediol. A second aliquot taken after an additional 2 hours contained no EpB, 3.72 weight percent 1,2-butenediol and 1.50 weight percent 1,4-butenediol. The remainder of the reaction mixture was filtered. The solid catalyst was washed with water and used to catalyze the hydrolysis of fresh solutions of 3,4-epoxy-1-butene two more times by the above procedure without noticeable loss of activity.

EXAMPLE 2

This example illustrates the use of a copper(II)-exchanged Y zeolite for the hydrolysis and the reuse of the recovered catalyst.

A pH 4 solution was prepared from copper sulfate pentahydrate (7.86 g) and water (4 liters). Zeolite NaY powder (40.0 g) was added to the stirred solution. The mixture was stirred for 2 hours and then filtered. The pH of the colorless filtrate was 7. The light blue solid was washed with water (200 mL) and dried overnight in an oven at 80° C. The zeolite contained 4.17 weight percent sodium and 4.56 weight percent copper as determined by inductively coupled plasma optical emission spectroscopy using a Perkin-Elmer Plasma 2000 instrument.

A portion of the zeolite catalyst (20 g) was slurried in water (200 ml). EpB (10.0 g) was added and the mixture was stirred as in Example 1. The initial temperature of the mixture was 24.5° C. and the temperature remained at this value for 25 minutes. After an additional 20 minutes, the temperature was 26.7° C. and a maximum temperature of 32.1° C. was achieved after an additional 20 minutes. After an additional 3 hours the temperature had fallen to 23.5° C., and the mixture was filtered. The pH 7 filtrate contained no detectable EpB, 3.72 weight percent 1,2-butenediol, 1.96 weight percent 1,4-butenediol.

The light green zeolite catalyst was washed with water (400 mL) and an identical fresh charge of water and EpB was added. The temperature rise was immediate upon addition of the EpB. The product was isolated in the same manner and contained no detectable EpB, 3.52 weight percent 1,2-butenediol and 1.86 weight percent 1,4-butenediol. The zeolite catalyst was washed on the filter with water (300 mL in portions) and dried on the filter at ambient temperature.

EXAMPLE 3

This example illustrates the beneficial effect of ammonia on the selectivity provided by a copper(II)-exchanged Y zeolite.

A solution was prepared from copper sulfate pentahydrate (7.86 g), water (4 liters) and concentrated aqueous ammonia (44 g). Zeolite NaY powder (40.0 g) was added to the stirred solution and stirring was continued for 2 hours. The zeolite catalyst was allowed to settle and then most of the liquid was decanted away. The pH of the nearly colorless decanted liquid was 11. The zeolite catalyst was reslurried in water (4 liters), stirred 30 minutes, allowed to settle, and most of the pH 10 liquid decanted away. The reslurring, stirring, settling and decantation procedure was repeated an additional time, and then the zeolite catalyst was filtered and washed on the filter with water (2 liters in portions). The pH of the final filtrate was 9. The zeolite catalyst then was dried overnight in an oven at 80° C. The catalyst contained 3.55 weight percent sodium and 4.93 weight percent copper.

A portion of the zeolite catalyst (20.0 g) was slurried in water (200 mL) and EpB (10.0 g) was added. The thermal behavior of the reaction was similar to that of Example 2 except that the thermal induction period was approximately 40 minutes. The reaction mixture was filtered 3 hours 20 minutes after the addition of the EpB. The pH 8 filtrate contained no detectable EpB, 2.78 weight percent 1,2-butenediol and 2.59 weight percent 1,4-butenediol.

EXAMPLE 4

This example illustrates the equilibration of a previously-used, copper-exchanged Y zeolite with ammonia and the improved selectivity observed with this catalyst in the hydrolysis of EpB.

An evaporating dish containing the catalyst recovered from Example 2 was placed in a desiccator containing concentrated aqueous ammonia solution. The catalyst was allowed to equilibrate with the vapor for seven hours and then removed from the desiccator and allowed to contact the ambient air overnight. The catalyst was slurried into water (200 mL) and EpB (10.0 g) was added. The reaction was allowed to proceed according to the procedure described in Example 2. The filtered product solution contained no detectable EpB, 2.62 weight percent 1,2-butenediol and 2.44 weight percent 1,4-butenediol.

EXAMPLE 5

This example illustrates the effect of replacement of the sodium ions in zeolite Y with both copper and another metal.

Zeolite NaY powder (100.0 g) was added a solution of lithium bromide (86.85 g) in water (4 liters). The mixture was stirred for 4 hours, allowed to settle and then most of the solution syphoned away from the settled zeolite. The exchange, settling and syphoning procedure was repeated two more times using fresh lithium bromide solution. After the final lithium bromide exchange, the zeolite was filtered, washed with water (1 liter in portions), and dried in an oven for seven days at 80° C. The zeolite was slurried in a solution prepared from copper sulfate pentahydrate (19.65 g) and water (4 liters). The mixture was stirred for 6 hours and then allowed to settle. The solution was syphoned away from the zeolite catalyst which was then filtered and washed with water (750 mL in portions). The catalyst was dried overnight at 80° C.

3,4-Epoxy-1-butene (10.0 g) was added to a slurry of a portion of the above-described zeolite catalyst (20.0 g) in water (200 ml) and the reaction was allowed to proceed as described in Example 2. The filtered product solution contained no detectable EpB, 3.79 weight percent 1,2-butenediol and 2.08 weight percent 1,4-butenediol. The recovered catalyst was washed with water (400 mL, in portions) and allowed to dry on the filter at room temperature.

EXAMPLE 6

This example illustrates the improvement in selectivity resulting from the treatment of recovered copper/lithium-exchanged zeolite Y with ammonia.

An evaporating dish containing the zeolite catalyst recovered from Example 5 was placed in a desiccator containing concentrated aqueous ammonia. The zeolite catalyst was allowed to equilibrate with the vapor for 6 hours and then removed from the desiccator and allowed to contact the ambient air overnight.

EpB (10.0 g) was added to a slurry of the above zeolite catalyst in water (200 mL) and the reaction was allowed to proceed as according to the procedure of Example 2. The filtered product solution contained no detectable EpB, 2.69 weight percent 1,2-butenediol and 2.59 weight percent 1,4-butenediol.

EXAMPLE 7

This example illustrates that prereduction of the copper zeolite catalyst eliminates the induction period which otherwise occurs.

A loosely-agglomerated sample of fresh copper-exchanged NaY zeolite (20.0 g) that did not pass a 20 mesh screen was loaded into a quartz tube. The sample was placed in a tube furnace and treated with 1 volume percent hydrogen in nitrogen at 200°–300° C. until the color of the entire catalyst color had changed from blue to white. The catalyst was allowed to cool to ambient temperature and then transferred under a nitrogen flow to a stirred mixture of 3,4-epoxy-1-butene (10.27 g) in water (200 mL). Upon contact of the catalyst with the water/EpB mixture the temperature rose from ambient temperature to 35.8° C. The temperature continued to rise over the next 2–3 minutes to 38.7° C. The reaction was stirred as described in Example 2 until the temperature had returned to ambient temperature (22.2° C.). The filtered product solution contained no EpB, 3.56 weight percent 1,2-butenediol and 2.08 weight percent 1,4-butenediol.

EXAMPLE 8

This example illustrates the effect of changing the zeolite framework structure.

Zeolite L powder (40.0 g) was added to a solution of copper sulfate pentahydrate (7.86 g) and water (4 liters) and the mixture was stirred for 3 hours. The zeolite catalyst was allowed to settle from the blue solution and most of the water was syphoned away from the catalyst. The zeolite catalyst was filtered, washed with water (200 mL, in portions) and dried over the weekend in an oven at 80° C. The light green zeolite catalyst contained 2.67 weight percent copper, 10.1 weight percent potassium and 77 parts per million (ppm) sodium.

EpB (10.0 g) was added to a slurry of a portion of the zeolite (20.0 g) in water (200 mL) and the reaction was allowed to proceed according to Example 2. The thermal induction period was 2 hours before the reaction exotherm occurred. The filtered product solution contained 0.02 weight percent EpB, 3.15 weight percent 1,2-butenediol and 1.88 wt % 1,4-butenediol.

COMPARATIVE EXAMPLE

This example illustrates how the use of copper in a soluble form is inferior to the process of the invention. EpB (10.0 g) was added to a solution of copper sulfate pentahydrate (2.4 g) in water (200 mL) and the mixture stirred according to the procedure described in Example 2. The unfiltered mixture contained no detectable EpB, 5.17 weight percent 1,2-butenediol and 0.58 weight percent 1,4-butenediol.

The invention has been described in detail with particular reference to preferred embodiments thereof, but it will be understood that variations and modifications can be effected within the spirit and scope of the invention.

I claim:

1. Process for the preparation of 1,4-butenediol which comprises contacting a mixture of water and 3,4-epoxy-1-butene with a supported copper catalyst comprising a catalyst support material and copper in a positive valence state.

2. Process according to claim 1 wherein water and 3,4-epoxy-1-butene are contacted at a temperature of about 10° to 80° C. in the presence of a supported copper catalyst comprising silica, alumina or silica-alumina and a copper(I) salt.

3. Process according to claim 2 wherein the mole ratio of water:3,4-epoxy-1-butene is in the range of about 20:1 to 5:1 and the supported catalyst comprises silica, alumina or silica-alumina, a copper(I) salt, and ammonia.

4. Process according to claim 1 wherein water and 3,4-epoxy-1-butene are contacted at a temperature of about 10° to 80° C. in the presence of a supported copper catalyst comprising a zeolite and a copper(I) or copper(II) salt.

5. Process according to claim 4 wherein the mole ratio of water:3,4-epoxy-1-butene is in the range of about 20:1 to 5:1 and the supported catalyst comprises a zeolite selected from faujasite-type and L-type zeolites and a copper(I) or copper(II) salt.

6. Process according to claim 5 wherein the supported catalyst comprises a zeolite selected from faujasite-type and L-type zeolites, a copper(I) salt, and ammonia.

7. Process according to claim 5 wherein the supported catalyst comprises a zeolite selected from faujasite-type and L-type zeolites and a copper(II) salt.

* * * * *